United States Patent [19]

Cates et al.

[11] Patent Number: 4,711,765
[45] Date of Patent: Dec. 8, 1987

[54] SORPTION/DESORPTION GAS ANALYSIS APPARATUS

[75] Inventors: Marion H. Cates; Eugene L. Szonntagh, both of Largo, Fla.

[73] Assignee: Honeywell Inc., Minneapolis, Minn.

[21] Appl. No.: 881,362

[22] Filed: Jul. 2, 1986

[51] Int. Cl.[4] .............. G01N 1/18; G01N 30/02; B01D 35/18; B01D 53/14
[52] U.S. Cl. .................... 422/89; 422/70; 422/88; 436/161; 436/167; 436/178; 55/179; 55/208; 55/390; 210/175; 210/198.3; 210/658
[58] Field of Search ............. 422/88, 89, 70; 436/161, 162, 178, 167; 55/34, 60, 77, 78, 179, 181, 190, 208, 390, 442, 444, 521, 529; 210/658 X, 198.3 X, 175 X

[56] References Cited

U.S. PATENT DOCUMENTS

| | | | |
|---|---|---|---|
| 3,110,581 | 11/1963 | Simpson | 55/444 X |
| 4,047,895 | 9/1977 | Urban | 422/177 |
| 4,207,084 | 6/1980 | Gardner | 55/189 X |
| 4,409,006 | 10/1983 | Mattia | 55/28 |
| 4,452,612 | 6/1984 | Mattia | 55/60 X |
| 4,534,777 | 8/1985 | Castleman et al. | 55/181 |
| 4,548,802 | 10/1985 | Dickey | 55/34 X |
| 4,548,803 | 10/1985 | Dickey | 55/34 X |
| 4,597,778 | 7/1986 | Szonntagh | 55/208 X |
| 4,599,095 | 7/1986 | Barnes et al. | 55/208 |
| 4,599,225 | 7/1986 | Dickey | 55/34 X |

FOREIGN PATENT DOCUMENTS 152721 11/1981 Japan .

Primary Examiner—Michael S. Marcus
Assistant Examiner—Lynn M. Kummert
Attorney, Agent, or Firm—M. J. Halista; A. Medved

[57] ABSTRACT

A sorption/desorption gas analysis apparatus includes a sorption/desorption bed having a thin layer of sorption material fixed to an outside surface of a first and a second adjacent tapered bed element arranged in a mutually mating configuration. The bed elements are further arranged to be selectively moved with respect to each other to produce a first flow volume therebetween past the sorptive material during a sorption mode of operation and a second substantially smaller flow volume past the sorptive material during a desorption mode of operation. The sorption/desorption bed is used in the gas analysis apparatus by first exposing the sorption bed to an impinging flow of a sample gas containing the constituent of interest which is sorbed by the sorptive material in the sorption mode of operation. During the desorption mode of operation, the first and second bed elements are displaced toward each other by a bed drive while flow directing elements are used to direct the flow of a desorbed sample from the sorption bed. Finally, the sorptive material is heated to desorb the sorbed sample and which is directed to an inlet of a detector, e.g., a gas chromatograph. The flow volume reduction provided by the volume of the flow path across the sorptive material during the desorption operation compared to the cumulative volume of impinging gas flow during the sorption operation produces a very high accumulation factor by minimizing the flow space volume.

20 Claims, 11 Drawing Figures

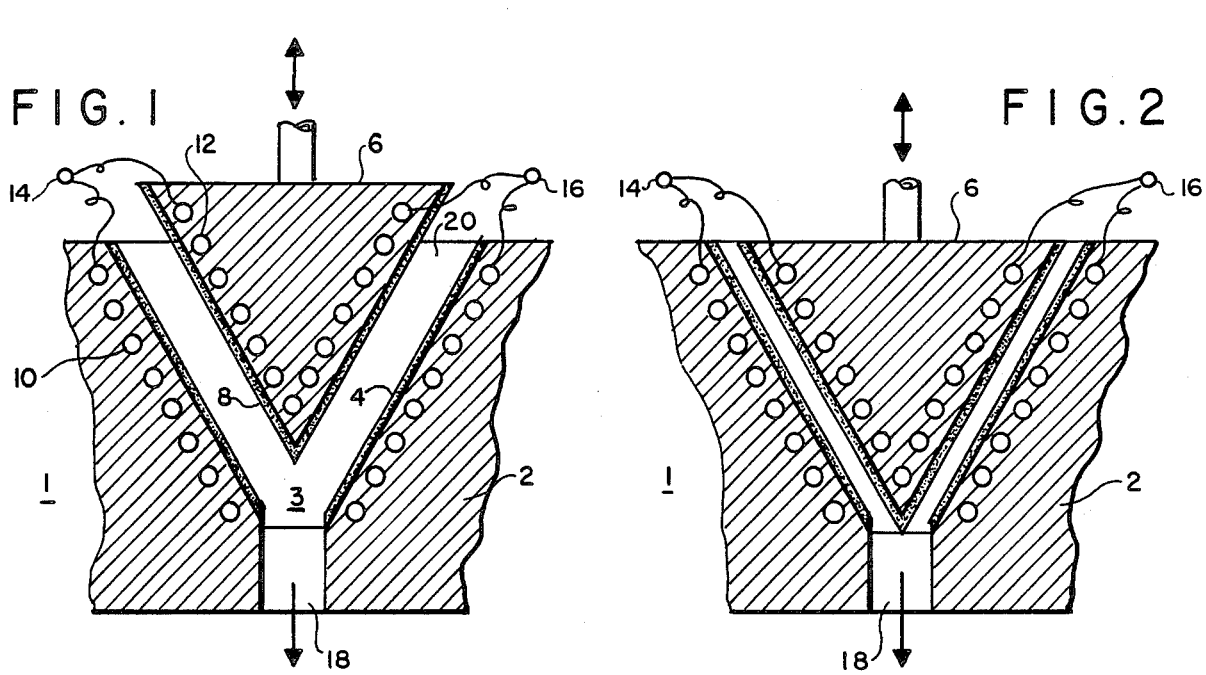
FIG. 1
FIG. 2
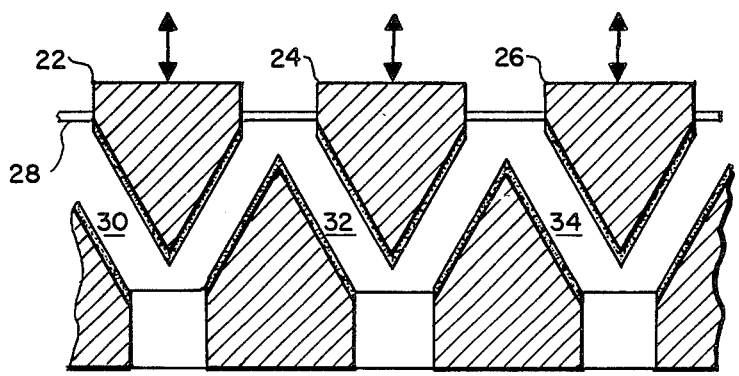
FIG. 3
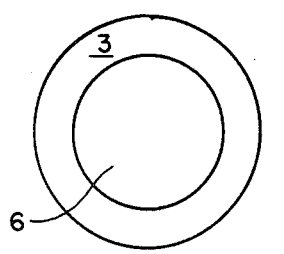
FIG. 4
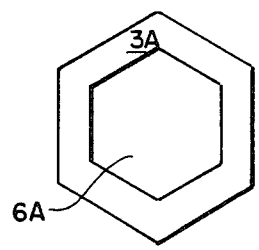
FIG. 5

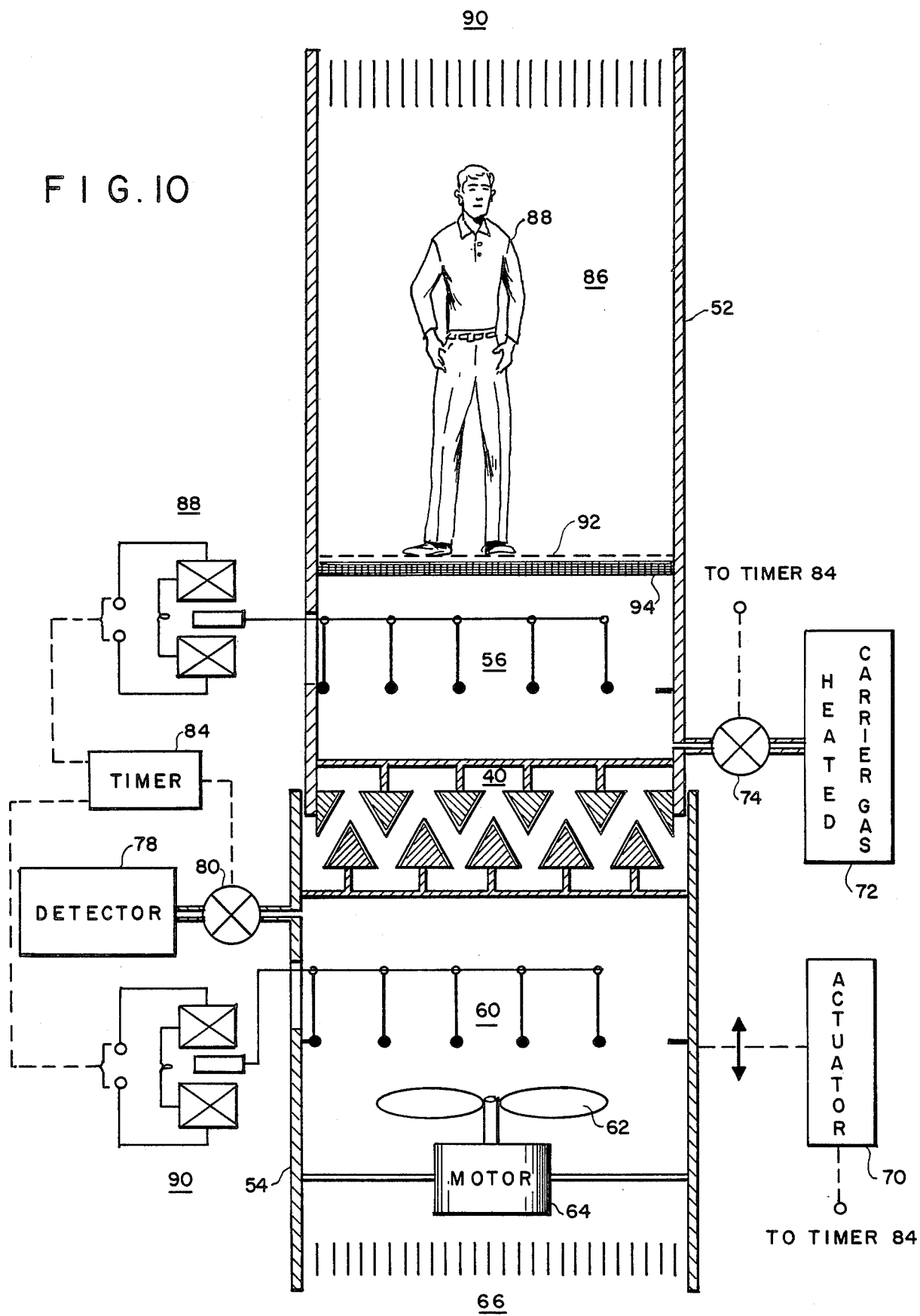

SORPTION/DESORPTION GAS ANALYSIS APPARATUS

BACKGROUND OF THE INVENTION

1. Field of the Invention

The present invention relates to gas analyzers. More specifically, the present invention is directed to a sorption/desorption gas analyzer apparatus.

2. Description of the Prior Art

Conventional sorption/desorption gas analyzer apparatus have employed sorption/desorption beds having a constant flow volume during the sorption/desorption cycle. Such sorption/desorption beds do not provide for a significant enhancement of the sensitivity of the gas analysis system since such sensitivity is strictly dependent on a constituent accumulation factor. Accordingly, to obtain a high sensitivity, it is critical to maximize the ratio of the sorption/desorption flow rates. The present invention provides a novel bed structure for maximizing such a ratio by utilizing substantial volume reduction during the desorption mode to affect the flow rate in a gas analyzer apparatus which is suitable for providing a gas analysis in a working environment.

SUMMARY OF THE INVENTION

An object of the present invention is to provide an improved sorption/desorption apparatus for a gas analyzer.

In accomplishing this and other objects, there has been provided, in accordance with the present invention a sorption/desorption analysis apparatus which includes a sorption/desorption bed means having a first tapered bed element and a tapered second bed element arranged to mate with the first bed element, inlet passage means for directing a fluid to be analyzed in a flow path across the bed means between the first and second bed elements to produce a sorption of the fluid to be analyzed by the sorption bed means, means for desorbing a sorbed sample from the bed means, detector means for receiving a desorbed sample from the bed means, means for directing a flow of a desorbed sample from said bed means to said detector means, drive means for selectively transferring the bed means between a high flow volume condition and a low flow volume condition by a relative movement of the first and second bed elements to produce a volume reduction in the fluid flow path across the bed means and a control means for operating the means for desorbing, the means for directing and the drive means.

BRIEF DESCRIPTION OF THE DRAWINGS

A better understanding of the present invention may be had when the following detailed description is read in connection with the accompanying drawings, in which:

FIG. 1 is a cross-sectional illustration of a sorption/desorption bed embodying an example of the present invention in a sorption mode of operation, FIG. 2 is a cross-sectional illustration of the bed shown in FIG. 1 in a desorption mode of operation, FIG. 3 is a cross-sectional illustration of a modified version of the bed shown in FIGS. 1 and 2, FIG. 4 is a top view of a first configuration of the sorption/desorption bed shown in FIGS. 1, 2 and 3, FIG. 5 is a top view of a second embodiment of the sorption/desorption bed shown in FIGS. 1, 2 and 3, FIG. 10 is a gas analysis operation embodying the apparatus shown in FIGS. 8 and 9 in a test station configuration and FIG. 11 is an alternate embodiment of the present invention in a hand-held example of a gas analysis apparatus.

DESCRIPTION OF THE PREFERRED EMBODIMENT

DETAILED DESCRIPTION

Figure 6:
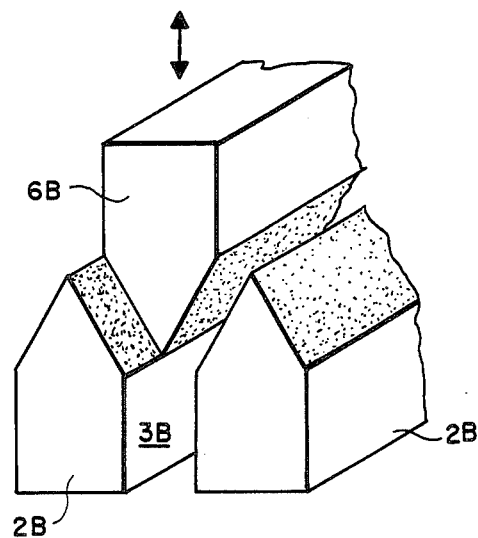
FIG. 6 is a pictorial illustration of a third embodiment of the sorption/desorption bed shown in FIGS. 1, 2 and 3.

Referring to FIG. 1 in more detail, there is shown a sorption/desorption bed 1 having a first bed element 2 providing a cone-shaped recess 3 wherein the wall of the recess 3 is coated with a sorptive material 4 and a second bed element 6 in the form of a cone coated with a sorptive material 8 and arranged to mate with the cone-shaped recess 3. The sorptive material 4,8 may be a fine powder, e.g., Carbopak, a graphitized carbon black, which is substantially uniformly deposited on a wet adhesive coating the bed elements 2,6 to form a thin coating, e.g., 0.1 mil, on the surface of the adhesive. The powder preferably has a maximum particle size of 100 mesh. Subsequently, the bed elements 2,6 are heat-cured to thoroughly dry the adhesive and fix the sorptive material 4,8 thereto. Heating elements 10 are embedded within the wall of the first bed element 2, i.e., adjacent to the recess 3, and similar heating elements 12 are embedded within the cone element. The heating elements 10,12 are connected to energizing terminals 14,16 for connection to a source of energizing electrical power (not shown). The heating elements 10,12 are arranged in close thermal association with respective ones of the sorptive material coatings 4,8 to provide a rapid heating thereof.

In the embodiment shown in FIGS. 1 and 2, the cone element 6 is arranged to be movable relative to the recess 2 element to provide a change in flow volume therebetween. The cone element 6 is shown in a sorption mode of operation in FIG. 1 and in a low flow volume desorption mode of operation in FIG. 2. The cone configuration of the bed elements 2,6 enables a small linear movement of the movable bed element to produce a large flow volume change. Additionally, by coating both surfaces of the cone 6 and the cone recess 3 with sorptive material, the slope of the cone increases the surface area of the sorptive material. For example, a 45° cone would produce about twice the surface area of a flat disc having the same diameter while sharper angles would produce even larger surface areas. The flow of a fluid over the sorptive material may be provided by suction from a suction pump connected to an outlet 18 of the recess 3 or by a source of pressurized carrier gas connected to supply a carrier gas to an inlet 20 of the recess 3. Further, instead of a unique carrier gas, the sample gas being analyzed could be used as a carrier gas.

While the sorption/desorption bed system shown in FIGS. 1 and 2 is illustrated as a single cone 6 and recess 3, it can be arranged as multiple cones and recesses as shown in FIG. 3. In this configuration, a plurality of cones 22,24,26 in the movable or upper row are fabricated in spaced apart locations on a common bar 28 while the lower series of recesses 30,32,34 in spaced locations to mate with the cones 22,24,26. While the cones 22,24,26 are illustrated as being movable, it should be noted that either of the bed elements can be moved to achieve a large gap and large flow volume for the sorption cycle and a small gap and small flow volume for the desorption cycle.

With the multiple cone system, the surface area or the sorption bed would be tremendously increased. For example, if one square inch base cones are used with a 9" length, the surface area will be fourteen times the original one square inch of a flat circular disc. If these cones are arranged on a 24" diameter tray forming a sorption/desorption bed, about two hundred of the one inch diameter cones can be utilized each having a surface area of fourteen square inches for a total of fifty six square inches. Thus, a flow rate fifty six hundred times the flow rate of the one square inch flat disc bed can be handled by the conical array. On the other hand, when desorbing, the volume of each cone gap can be ten microliters which would provide a total desorption volume for the two hundred cones of two milliliters.

Figure 7:
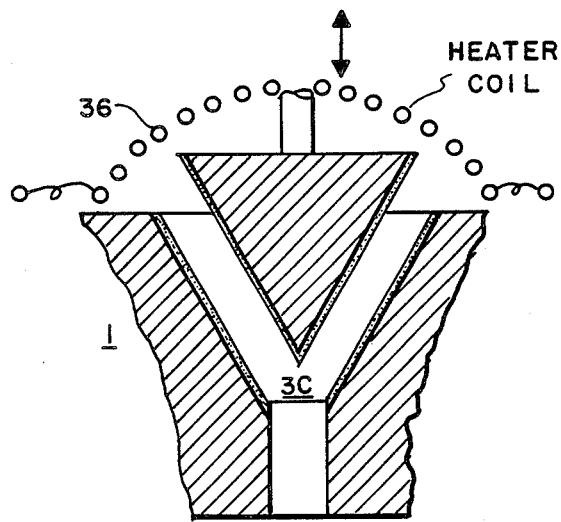
FIG. 7 is an alternate embodiment of the bed shown in FIGS. 1 and 2 with an external heating coil.

In addition to the convenient and effective volume changing method, the aforesaid basic cone construction has the advantage of being organized into different geometrical configurations. For example, FIG. 4 shows a top view of a circular cone 6 and circular cone-shaped recess 3 while FIG. 5 shows a hexagonal cone 6A and hexagonal mating recess 3A. Further, FIG. 6 shows a wedge configuration of the bed elements utilizing an upper wedge 6B and lower wedges 2B to form a wedge-shaped recess 3B. While in FIGS. 1 and 2, there has been shown a heating of the sorption/desorption bed 1 during the desorption cycle by embedded heating elements 10,12, the heating may be achieved either by heating the incoming air or carrier gas by hot wires arranged at the entrance of the bed flow volume or by providing a heated carrier gas supply. In FIG. 7, there is shown an arrangement using a heater coil 36 at the entrance to the flow volume or recess 3C of the sorption/desorption bed 1.

Figure 8:
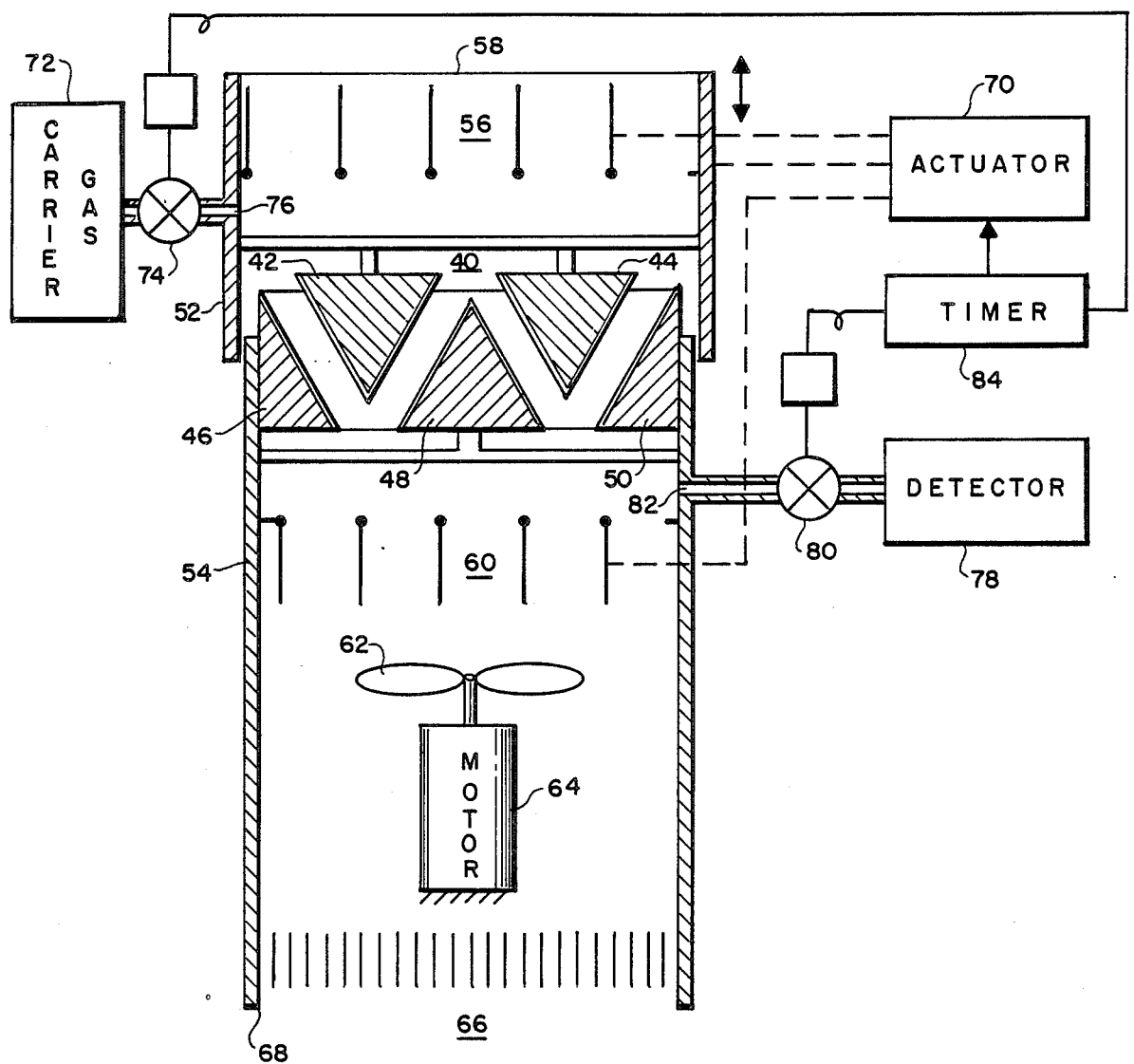
FIG. 8 is a pictorial illustration of a gas analysis apparatus embodying an example of the present invention in a sorption mode of operation.

In FIG. 8, there is shown an embodiment of the present invention in an operative example of a gas analyzing apparatus. In this apparatus, a sorption/desorption bed 40 would use a plurality of cones 42,44 and recess elements 46,48,50 arranged transversely across the interior of a support cylinder in the form of a telescoping first and second cylinders 52,54 with the first cone bed elements 42,44 connected to the first cylinder 52 and the second bed elements or recess elements 46,48,50 being connected to the second cylinder 54. Thus, as the second cylinder 54 is telescoped within the first cylinder 52, the flow volume is reduced by having the first bed elements 42,44 displaced toward the second bed elements 46,48,50. A first plurality of vanes or shutters 56 are arranged across the diameter of the first cylinder 52 adjacent to first bed elements 42,44 and are pivoted to provide directional flow control or guidance in an open state for a fluid entering an open end 58 of the first cylinder 52 and to cut off the flow in a closed state. A second plurality of vanes or shutter elements 60 are provided in the second cylinder 54 on the other side of the sorption/desorption bed 40 from the first shutters 56 and are similarly arranged to be selectively actuated to provide either flow path guidance and flow path cut-off. A motor-driven fan 62 attached to an output shaft of a motor 64 is provided within the second cylinder 54 on the other side of the second set of vanes 60 from the sorption/desorption bed 40 to induce an air flow over the bed 40 during the sorption mode of operation. Finally, a plurality of parallel flow guidance fins 66 are provided in an exit end 68 of the second cylinder 54 following the motor 64 and fan 62 to provide an exit for the air driven by the fan 62.

An actuator apparatus 70 is arranged to provide an actuation or pivoting motion of the first and second shutters 56,60 and to provide a telescoping motion of the first and second cylinders 52,54 to effect a relative motion of the first bed elements 42,44 and the second bed elements 46,48,50, such actuators being well-known in the art. A carrier gas source 72 is connected through an electrically controlled valve 74 to an inlet 76 on the first cylinder 52 between the first shutters 56 and the first elements 42,44 of the bed 40. Similarly, a gas detector 78, e.g., a gas chromatograph, is connected through a second electromagnetically controlled valve 80 to a outlet 82 from the second cylinder 54 between the second bed elements 46,48,50 and the second shutters 60. A timer 84 is arranged to control the valves 74,78 and the actuator 70 to provide an operation of the gas analyzing apparatus between a sorption and desorption mode of operation.

The position of the elements in the gas analyzing apparatus shown in FIG. 8 is that used in a sorption mode of operation wherein the first bed elements 42,44 and second bed elements 46,48,50 are positioned apart from each other to maximize the flow volume through the bed 40, and the first and second shutters 56,60 are in an opened state. At this time, the valves 74,80 are closed to prevent the carrier gas from issuing from the carrier gas source 72 and to isolate the detector 78. As a result, the fan 62 driven by the motor 64 is effective to produce a maximum flow past the first shutters 56, through the first and second elements of the bed 40 and past the second set of shutters 60 to the exit 68 of the second cylinder 54.

Figure 9:
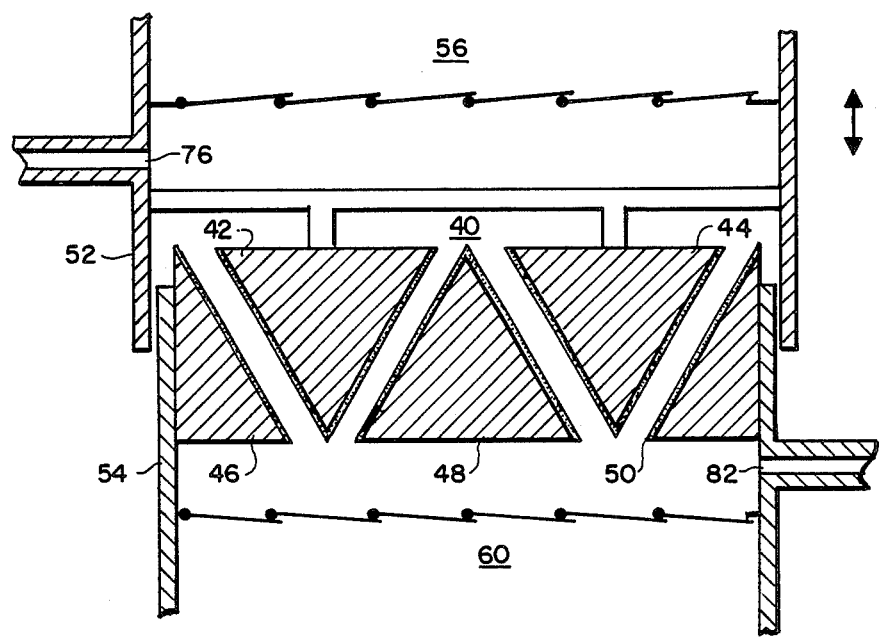
FIG. 9 is a partial illustration of the apparatus shown in FIG. 8 in a desorption mode of operation.

During a desorption mode of operation, the position of the elements of the apparatus are shown in FIG. 9. Thus, the first and second cylinders 52,54 are telescoped within one another by an operation of the actuator 70 to move the first bed elements 42,44 and second bed elements 46,48,50 toward each other and to reduce the flow volume of therebetween. Concurrently, the first and second set of shutters 56,60 are closed by the actuator 70 and the valves 74,80 are opened by the timer 84 to permit the flow of the carrier gas from the source of carrier gas 72 through the restricted flow volume of the bed 40 to the detector 78. During the desorption cycle, the bed 40 is heated to desorb the adsorbed sample, e.g., by heater wires in the bed elements, by heater wires at the inlet to the bed 40 or by a heated source of carrier gas. The desorbed sample is swept by the carrier gas into the detector 78 to be analyzed.

In FIG. 10, there is shown an embodiment of the present invention in a test station configuration. Similar reference numbers have been used to designate elements found in FIGS. 8 and 9. The gas analyzing apparatus shown in FIG. 10 includes a compartment 86 providing a fixed volume for housing a test subject 88. This compartment is formed by an extension of the second cylinder 52 described above with respect to FIGS. 8 and 9. A second plurality of parallel flow guidance fins 90 are provided at an inlet to the compartment 86 to guide the incoming air flow. A perforated floor 92 is provided within the compartment 86 to support the test subject 88. A filter 94 may be located beneath the floor 92 to provide filtering of dust particles, etc. Inasmuch as the cylinder 82 would provide the compartment for the test subject 88, it is preferable in the embodiment shown in FIG. 10 to move the second cylinder 54 to reduce the flow volume between the elements of the bed 40. Accordingly, the actuator 70 is shown as being connected to the second cylinder 54. Further, the operation of the valves 74 and 80 are arranged to be directly operated by the timer 84 while the shutters 56 and 60 are also shown with an electromagnetic actuator 88 and 90 which are directly operated by the timer 84. Finally, the carrier gas source 72 is shown as heated source to provide a heating of the sorption/desorption bed 40. The operation of the apparatus shown in FIG. 10 is similar to that described above with respect to FIGS. 8 and 9 with the exception that the second cylinder 54 is moved by the actuator 70 to bring together the elements of the bed 40. Thus, after a sample is adsorbed by the bed 40 from the compartment 86, the cylinders 52,54 are telescoped, the shutters 56 and 60 are closed and the valves 74 and 80 are opened to desorb the sample by the heated carrier gas from the bed 40 into the detector 78.

Figure 11:
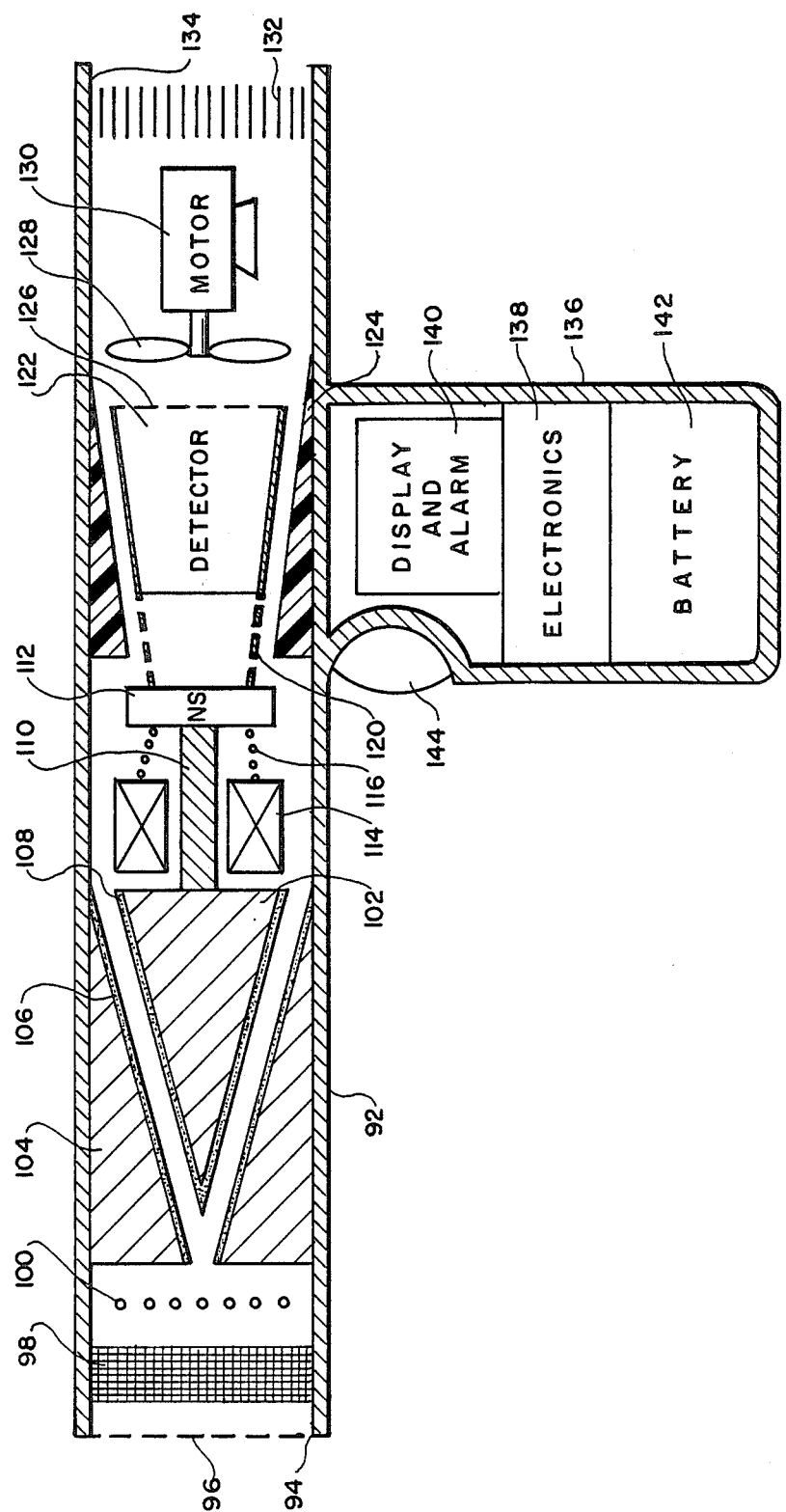

In FIG. 11, there is shown a hand-held example of the gas analyzing apparatus of the present invention. The pistol-shaped housing 92 includes an inlet 94 having a screen 96 thereacross. A filter element 98 is provided across the inlet 94 behind the screen 96. Heater wires 100 are located between the filter 98 and the inlet of a sorption/desorption bed having a cone-shaped first bed element 102 and a recess element 104. The recess element 104 is affixed to a interior surface of the housing 92 to limit the flow volume across the sorptive material 106 on the surface of the recess element 104 and the sorptive material 108 on the surface of the cone element 102. The cone element 102 is attached by a rigid bar 110 to a magnetic plate 112. The bar 110 is arranged to pass through the center of a coaxial solenoid coil 114. A spring 116 is located between the coil 114 and the magnetic plate 112 to act as a return spring.

On the other side of the magnetic plate 112 from the spring 116, a partially perforated housing 120 containing a gas constituent detector 122 is attached to the plate 112. The housing 120 is arranged in a tapered form with an unperforated longitudinal portion arranged to mate with a tapered recess forming element 124 attached to an inner surface of the housing 92. The outlet of the perforated housing 124 is provided with a perforated screen 126. A fan 128 driven by a motor 130 is located within the housing 92 facing the perforated exit screen 126 of the detector 122. A plurality of parallel flow guidance fins 132 are provided in an exit port 134 of the housing 92. A pistolgrip extension 136 of the housing 92 is arranged to house an electronic circuit 138 for operating the solenoid coil 114, the detector 122 and a display and alarm circuit 140. A battery 142 for providing electrical power to the electronic circuit 138, and the display and alarm circuit 140 is also contained within the pistolgrip housing 136. Finally, a trigger 144 is located in the pistolgrip housing 136 to provide an operator-controlled means for effecting the operation of a gas analyzing apparatus. The internal wiring interconnecting the various elements of the apparatus shown in FIG. 11 have been omitted in the illustration for purposes of clarity.

The position of the elements of the apparatus shown in FIG. 11 are illustrated in a sorption mode of operation wherein the cone element 102 is displaced from the recess element 104 by the spring 116 to provide a maximum flow volume past the sorptive material 106, 108. Additionally, the solenoid 114 is deenergized, and the spring 116 urges the detector housing 120 away from the recess element 124 to provide a flow bypass path around the outside of the housing 120. This low resistance bypass flow path enables the flow induced by the fan 128 to bypass the interior of the housing 120, i.e., the flow is directed away from the detector 122. In a desorption mode of operation the trigger 144 is operated, and the solenoid 144 is energized. The energization of the solenoid 144 is effective to attract the magnetic plate 112 against the force of the return spring 116. This motion of the magnetic plate 112 produces a movement of the cone element 102 toward the recess element 104 to minimize the flow volume therebetween. Additionally, the housing 120 is drawn against the recess element 124 to force the flow induced by the fan 128 through the perforated screen inlet of the housing 120. Additionally, the heater wires 100 are energized to heat the incoming air which acts as the carrier gas. The electronic circuit 138 is actuated to control an operation of the detector and a display of the detected constituent by the display and alarm circuit 140. Upon a release of the trigger 144, the solenoid 114 is deenergized, and the return spring 116 is effective to displace the magnetic plate 112 and withdraw the cone element 102 from the recess element 104. Concurrently, the detector housing 120 is displaced from the recess element 124 to provide the bypass path for the flow past the detector 122 and housing 120. Thus, the apparatus shown in FIG. 11 is selectively actuated to provide a detection operation by changing the sorption mode of operation to a desorption mode of operation.

Accordingly, it may be seen that there has been provided, in accordance with the present invention an improved gas analyzing apparatus.

The embodiments of the present invention in which an exclusive property or privilege is claimed are defined as follows:

1. A sorption/desorption analysis apparatus comprising
sorption/desorption bed means having a first tapered bed element and a second tapered bed element arranged to mate with said first bed element said first and second tapered bed elements forming a fluid flow path therebetween,
inlet passage means for directing a fluid to be analyzed to said flow path across said bed means between said first and second bed elements to produce a sorption of the fluid to be analyzed by the sorption bed means,
means for desorbing a sorbed sample from said bed means detector means for receiving and analyzing a desorbed sample from said bed means,
means for directing a flow of a desorbed sample from said bed means to said detector means,
drive means for displaying and second bed element relative to said first bed element for selectively transferring said bed means from a high flow volume condition during a sorption operation to a low flow volume condition during a desorption operation by a relative movement of said first and second bed elements to produce a volume reduction in the fluid flow path across said bed means and means for operating said means for desorbing, said means for directing and said drive means to transfer the apparatus between the sorption operation and the desorption operation.

2. An apparatus as set forth in claim 1 wherein said means for directing includes a gas outlet passage means for directing the flow of the desorbed sample.

3. An apparatus as set forth in claim 1 wherein said means for desorbing includes heater means for heating said bed means.

4. An apparatus as set forth in claim 1 wherein said desorbing means includes a fan means for urging a fluid flow past said bed means during the sorption and desorption operations.

5. An apparatus as set forth in claim 1 wherein said first bed element is a circular cone.

6. An apparatus as set forth in claim 1 wherein said first bed element is an hexagonal cone.

7. An apparatus as set forth in claim 1 wherein said means for operating is arranged to concurrently operate said means for desorbing, said means for directing and said drive means.

8. An apparatus as set forth in claim 1 wherein said means for directing includes bypass path means for selectively providing a bypass flow path past said detector means.

9. An apparatus as set forth in claim 8 wherein said bypass path means includes a movable housing for said detector means and an external container for said housing cooperating with said housing to define said bypass flow path.

10. An apparatus as set forth in claim 9 wherein said means for operating includes an electromagnetic solenoid having a movable armature connected to said housing and to said bed means for producing a concurernt movement thereof.

11. An apparatus as set forth in claim 1 wherein said means for directing includes shutter means for isolating said bed means from said inlet means.

12. An apparatus as set forth in claim 11 wherein said means for directing includes second shutter means for defining a flow path to said detector means.

13. An apparatus as set forth in claim 12 wherein said means for desorbing includes a selectively operable carrier gas source means arranged to urge a desorbed sample from said bed means to said detector means.

14. An apparatus as set forth in claim 13 wherein said carrier gas source means provides a heated carrier gas.

15. An apparatus as set forth in claim 13 wherein the carrier gas source means provides a carrier gas which is heated before reaching said bed means.

16. An apparatus as set forth in claim 1 wherein said bed means includes a first cylinder supporting said first bed element and a second cylinder arranged to be telescoped within said first cylinder while supporting said second element and said drive means is arranged to telescope said first cylinder and said second cylinder to effect the relative movement of the first and second bed elements.

17. An apparatus as set forth in claim 16 wherein said means for directing includes first shutter means within said first cylinder for isolating said bed means from said inlet means.

18. An apparatus as set forth in claim 17 wherein said means for directing includes second shutter means within said second cylinder for isolating said bed means for defining a flow path to said detector means.

19. An apparatus as set forth in claim 18 wherein said means for desorbing includes heater means for heating a fluid flowing across said bed means during the desorption operation.

20. An apparatus as set in claim 19 wherein said heater means is arranged to heat a fluid flowing across said bed means during the desoprtion operation before the fluid reaches said bed means.

* * * * *